United States Patent
Shimkets et al.

(10) Patent No.: US 11,492,397 B2
(45) Date of Patent: Nov. 8, 2022

(54) NEUTRALIZING MONOCLONAL ANTIBODIES TO IL-25 AND USES THEREOF

(71) Applicant: ABEOME CORPORATION, Athens, GA (US)

(72) Inventors: Richard A. Shimkets, Commerce, GA (US); Crystal Lyles Jackson, Jefferson, GA (US); Nathan Bartlett, Wallsend (AU); Thomas Vincent, Athens, GA (US); Yonghua Luo, Athens, GA (US)

(73) Assignee: ABEOME CORPORATION, Athens, GA (US)

( * ) Notice: Subject to any disclaimer, the term of this patent is extended or adjusted under 35 U.S.C. 154(b) by 434 days.

(21) Appl. No.: 16/085,871

(22) PCT Filed: Mar. 9, 2017

(86) PCT No.: PCT/US2017/021578
§ 371 (c)(1),
(2) Date: Sep. 17, 2018

(87) PCT Pub. No.: WO2017/160587
PCT Pub. Date: Sep. 21, 2017

(65) Prior Publication Data
US 2020/0291105 A1    Sep. 17, 2020

Related U.S. Application Data

(60) Provisional application No. 62/309,135, filed on Mar. 16, 2016.

(51) Int. Cl.
*A61K 39/395* (2006.01)
*C07K 16/24* (2006.01)
*A61K 39/00* (2006.01)

(52) U.S. Cl.
CPC ........ *C07K 16/244* (2013.01); *A61K 39/3955* (2013.01); *A61K 2039/505* (2013.01); *C07K 2317/565* (2013.01); *C07K 2317/76* (2013.01)

(58) Field of Classification Search
CPC .............. C07K 16/244; C07K 2317/56; C07K 2317/76; A61K 2039/505; A61K 39/3955
See application file for complete search history.

(56) References Cited

U.S. PATENT DOCUMENTS

| | | |
|---|---|---|
| 7,977,461 B2 | 7/2011 | Takayama et al. |
| 8,057,794 B2 | 11/2011 | Rapecki et al. |
| 2011/0287444 A1 | 11/2011 | Kanamori et al. |
| 2011/0311552 A1 | 12/2011 | Gurney et al. |
| 2011/0318353 A1 | 12/2011 | Almagro et al. |
| 2013/0251723 A1 | 9/2013 | Rohlff et al. |
| 2015/0316552 A1 | 11/2015 | Cain et al. |

FOREIGN PATENT DOCUMENTS

| | | |
|---|---|---|
| CN | 101711256 A | 5/2010 |
| CN | 102245638 A | 11/2011 |
| CN | 103097416 A | 5/2013 |
| JP | 2010-524450 A | 7/2010 |
| JP | 2012-507543 A | 3/2012 |
| KR | 2010-0021569 A | 2/2010 |
| WO | 2007044450 A2 | 4/2007 |
| WO | 2008129263 A1 | 10/2008 |
| WO | 2010038155 A1 | 4/2010 |
| WO | 2010051307 A1 | 5/2010 |
| WO | 2011054007 A1 | 5/2011 |
| WO | 2012175691 A1 | 12/2012 |

OTHER PUBLICATIONS

Witowski et al. "Interleukin-17: a mediator of inflammatory responses". Cell and Molecular Life Sciences, 61 (2004) 567-579 (Year: 2004).*
Asquith and McInnes. "Emerging cytokine targets in rheumatoid arthritis". Current Opinion in Rheumatology: May 2007—vol. 19—Issue 3—p. 246-251. (Year: 2007).*
Tang et al. "IL-25 promotes the function of CD4+CD25+ T regulatory cells and prolongs skin-graft survival in murine models". International Immunopharmacology 28 (2015) 931-937. (Year: 2015).*
Mantani et al. "IL-25 Inhibits Atherosclerosis Development in Apolipoprotein E Deficient Mice". PLoS ONE 10(1): e0117255 (2015) p. 1-18. (Year: 2015).*
Senra et al. "Keratinocyte-Derived IL-17E Contributes to Inflammation in Psoriasis". Journal of Investigative Dermatology (2016) 136, 1970-1980. (Year: 2016).*
Mombelli et al. "IL-17A and its homologs IL-25/IL-17E recruit the C-RAF/S6 kinase pathway and the generation of pro-oncogenic LMW-E in breast cancer cells". Scientific Reports vol. 5, Article No. 11874 (2015) (Year: 2015).*
Corrigan et al. "T-helper cell type 2 (Th2) memory T cell-potentiating cytokine IL-25 has the potential to promote angiogenesis in asthma". PNAS, Jan. 25, 2011, vol. 108, No. 4, p. 1579-1584. (Year: 2011).*
DSI. "Lung Fibrosis".2016 archived version accessed May 20, 2021 from web.archive.org/web/20160529052826/https://www.datasci.com/solutions/respiratory/lung-fibrosis (Year: 2016).*
Rapaka and Kolls. "Pathogenesis of allergic bronchopulmonary aspergillosis in cystic fibrosis: current understanding and future directions"; Medical Mycology 2009 (Supplement 1), S331-S337 (Year: 2009).*
Brown et al. "Tolerance of single, but not multiple, amino acid replacements in antibody VH CDR2: a means of minimizing B cell wastage from somatic hypermutation?" J Immunol 1996; 156:3285-3291 (Year: 1996).*

(Continued)

*Primary Examiner* — Xiaozhen Xie
(74) *Attorney, Agent, or Firm* — Meunier Carlin & Curfman LLC

(57) ABSTRACT

Disclosed are compositions and methods related to IL-25 binding molecules.

8 Claims, 8 Drawing Sheets
Specification includes a Sequence Listing.

(56) References Cited

OTHER PUBLICATIONS

Jin, W et al., "IL-17 cytokines in immunity and inflammatiion", Emerging Microbes and Infections, vol. 2, e60, DOI:10.1038/emi.2013.58;, Sep. 18, 2013, p. 1 first column, first paragraph.

NCBI Reference Sequence XP_01269, Prediticted: Low Quality Protein: heterogeneous nuclear ribonucleoprotein A/B-like, Jun. 12, 2015.

International Search Report and Written Opinion issued in related International Application No. PCT/US2017/021578 dated Aug. 28, 2017.

Younesi, Vahid, and Foroogh Nejatollahi. "Induction of anti-proliferative and apoptotic effects by anti-IL-25 receptor single chain antibodies in breast cancer cells." International immunopharmacology 23.2 (2014): 624-632.

Ballantyne, Sarah J., et al. "Blocking IL-25 prevents airway hyper-responsiveness in allergic asthma." Journal of Allergy and Clinical Immunology 120.6 (2007): 1324-1331.

Camelo, Ana, et al. "Blocking IL-25 signalling protects against gut inflammation in a type-2 model of colitis by suppressing nuocyte and NKT derived IL-13." Journal of gastroenterology 47.11 (2012): 1198-1211.

Extended European Search Report issued for European Application No. 17767186.4, dated Sep. 25, 2019, 11 pages.

International Preliminary Report on Patentability issued for Application No. PCT/US2017/021578, dated Sep. 27, 2018.

Office Action issued in corresponding European Application No. 17767186.4, dated Jan. 21, 2021, 6 pages.

Office Action issued in corresponding Japanese Application No. 2019-500220, dated Mar. 16, 2021.

Office Action issued in corresponding Eurasian Application No. 201892096/28, dated Nov. 27, 2018, 4 pages.

Office Action issued in corresponding Japanese Application No. 2019-500220, dated Nov. 2, 2021.

Notification of Refusal issued in corresponding Korean Application No. 10-2018-7029830, dated Dec. 14, 2021.

Office Action issued in corresponding Chinese Application No. 201780030583.4, dated Aug. 9, 2021.

\* cited by examiner

| Clone | $K_{on}$ | $K_{off}$ | $K_D$ |
|---|---|---|---|
| | $M^{-1}s^{-1}$ | $s^{-1}$ | $pM$ |
| ABM 109.2 against human IL-25 | $1.50 \times 10^6$ | $3.72 \times 10^{-5}$ | 24 |
| ABM 109.2 against mouse IL-25 | $7.16 \times 10^5$ | $2.06 \times 10^{-5}$ | 28 |
| ABM 109 vs human IL-25 | $9.85 \times 10^5$ | $3.78 \times 10^{-6}$ | 4 |

FIG. 9

IL-25 Neutralization – IC$_{50}$

| mAb | human | mouse |
|---|---|---|
| ABM125 | 0.97 nM | 2.4 nM |
| hABM125.9 | 0.95 nM | 5.9 nM |
| hABM125.10 | 1.5 nM | 4.9 nM |

Affinity (SPR)

| mAb | human IL-25 (HEK) | | | mouse IL-25 (NS0) | | |
|---|---|---|---|---|---|---|
| | k$_{on}$ (M$^{-1}$s$^{-1}$) | k$_{off}$ (s$^{-1}$) | K$_D$ (pM) | k$_{on}$ (M$^{-1}$s$^{-1}$) | k$_{off}$ (s$^{-1}$) | K$_D$ (nM) |
| ABM125 | 9.18 × 10$^4$ | 4.85 × 10$^{-7}$ | 5.3 | 1.34 × 10$^5$ | 9.85 × 10$^{-7}$ | 7.3 |
| hABM125.9 | 2.20 × 10$^6$ | 1.35 × 10$^{-4}$ | 61 | 7.87 × 10$^5$ | 5.77 × 10$^{-4}$ | 733 |
| hABM125.10 | 2.50 × 10$^6$ | 9.35 × 10$^{-6}$ | 374 | 8.37 × 10$^4$ | 8.91 × 10$^{-5}$ | 1065 |

NEUTRALIZING MONOCLONAL ANTIBODIES TO IL-25 AND USES THEREOF

I. BACKGROUND

Interleukin-25 (IL-25), also known as IL-17E, is a cytokine that belongs to the IL-17 cytokine family and is secreted by type 2 helper T cells (Th2) and mast cells. IL-25 induces the production of other cytokines, including IL-4, IL-5 and IL-13, in multiple tissues and stimulates the expansion of eosinophils.

IL-25 has been implicated in chronic inflammation associated with the gastrointestinal tract and the IL-25 gene has been identified in a chromosomal region associated with autoimmune diseases of the gut, such as inflammatory bowel disease (IBD). Conventional therapies for treatment of IBD involve either antibiotics or steroid-derived drugs; however these are not currently successful in inducing or maintaining clinical remission in patients.

IL-25 has also been shown to be unregulated in samples from patients with asthma, a condition estimated to affect more than 300 million people worldwide; suggesting that overexpression of this cytokine contributes to the pathology of asthma and related conditions.

Thus, there is a need for effective antagonists of IL-25 that are useful in the treatment of diseases and conditions characterized by IL-25 overexpression, including asthma and inflammatory bowel disease.

II. SUMMARY

Disclosed herein, in one aspect, are binding molecules directed to IL-25 that suitable for use in the treatment of IL-25 mediated diseases and disorders.

In one aspect, disclosed herein are isolated IL-25 binding molecules comprising a heavy chain variable domain comprising one or more Complementary Determining Regions (CDR)s as set forth in SEQ ID NO: 1, SEQ ID NO: 2, SEQ ID NO: 3, SEQ ID NO: 7, SEQ ID NO: 8, and SEQ ID NO: 9, Also disclosed are IL-25 binding molecules comprising a heavy chain variable domain wherein the heavy chain variable domain comprises SEQ ID NO: 13 and SEQ ID NO 15

In one aspect, disclosed herein are light chain variable domains comprising one or more CDRs as set forth in SEQ ID NO: 4, SEQ ID NO: 5, SEQ ID NO: 6, SEQ ID NO: 10, SEQ ID NO: 11, and SEQ ID NO: 12.

Also disclosed herein are isolated IL-25 binding molecules comprising a light chain variable domain wherein the light chain variable domain comprises SEQ ID NO: 14, SEQ ID NO 16;

In one aspect the disclosed IL-25 binding molecules can comprise both a heavy chain variable domain and a light chain variable domain or complementary determining regions (CDRs) of any preceding aspect.

Accordingly, disclosed herein are IL-25 binding molecules comprising one, two, or three of the heavy chain variable domains CDRs selected from the group comprising SEQ ID NO: 1, SEQ ID NO: 2, SEQ ID NO: 3, SEQ ID NO: 7, SEQ ID NO: 8, and SEQ ID NO: 9, and one, two, or three of the light chain variable domains CDRs selected from the group comprising SEQ ID NO: 4, SEQ ID NO: 5, SEQ ID NO: 6, SEQ ID NO: 10, SEQ ID NO: 11, and SEQ ID NO: 12

Also disclosed herein are IL-25 binding molecules comprising a heavy chain variable domain wherein the heavy chain variable domain comprises SEQ ID NO: 13 or SEQ ID NO 15, and a light chain variable domain wherein the light chain variable domain comprises SEQ ID NO: 14 or SEQ ID NO 16.

Further disclosed herein are humanized IL-25 binding molecules comprising a heavy chain variable domain wherein the heavy chain variable domain comprises SEQ ID NO: 17 and a light chain variable domain wherein the light chain variable domain comprises SEQ ID NO: 18.

In one aspect, disclosed herein are methods of treating, inhibiting, or preventing a rhinoviral infection airway inflammation, rheumatoid arthritis, osteoarthritis, bone erosion, intraperitoneal abscesses and adhesions, inflammatory bowel disorder, allograft rejection, psoriasis, certain types of cancer, angiogenesis, atherosclerosis, cystic fibrosis and multiple sclerosis comprising administering a therapeutic amount of any of the IL-25 binding molecules of any preceding aspect.

III. BRIEF DESCRIPTION OF THE DRAWINGS

The accompanying drawings, which are incorporate in and constitute a part of this specification, illustrate several embodiments and together with the description illustrate the disclosed compositions and methods.

FIG. 9 shows the potency and binding affinity of humanized (CDR-grafted) versions of ABM125, referred to as ABM125.9 and ABM125.10, compared with the chimeric ABM125 with fully mouse variable regions.

IV. DETAILED DESCRIPTION

Figure 1:
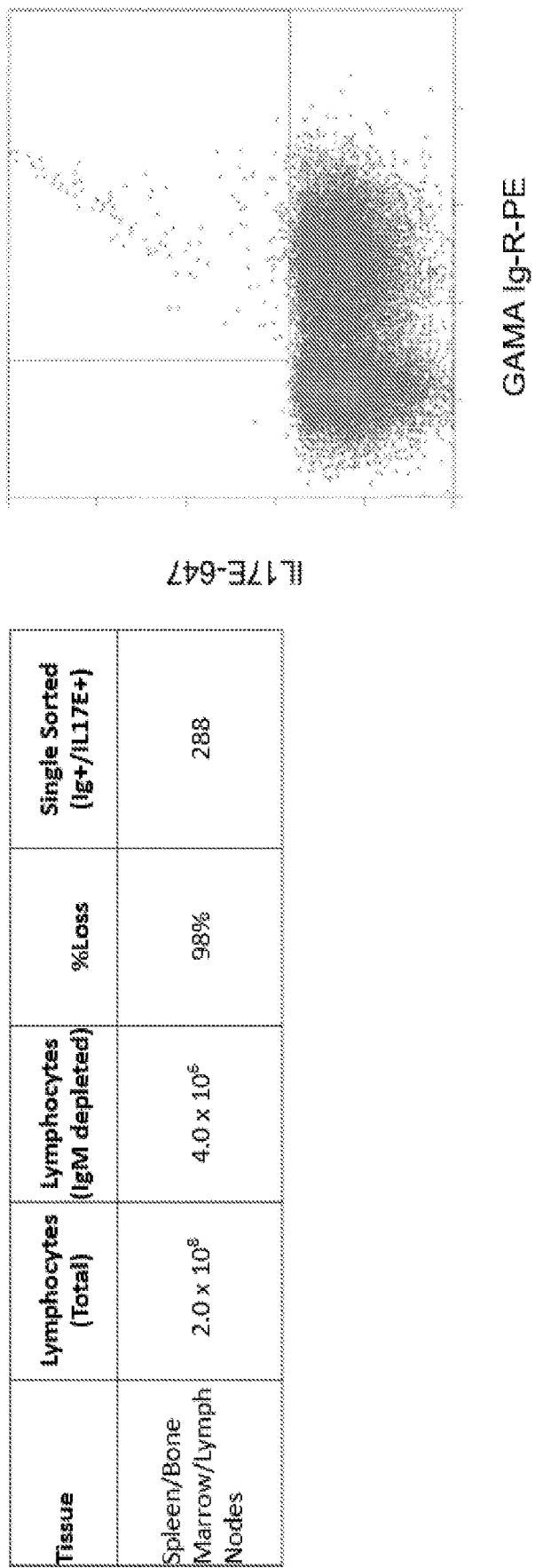
FIG. 1 shows a summary of B cells removed from a mouse immunized with IL-25 and their fluorescence sort plot of B cells binding to IL-25.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular anti-IL-25 antibody is disclosed and discussed and a number of modifications that can be made to a number of molecules including the anti-IL-25 antibody are discussed, specifically contemplated is each and every combination and permutation of an anti-IL-25 antibody and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

As noted above, increased levels of IL-25 have been associated with several conditions, diseases or disorders including airway inflammation, rheumatoid arthritis ("RA"), osteoarthritis, bone erosion, intraperitoneal abscesses and adhesions, inflammatory bowel disorder ("IBD"), cystic fibrosis, allograft rejection, psoriasis, certain types of cancer, angiogenesis, atherosclerosis and multiple sclerosis ("MS").

The IL-17 family of cytokines presently includes IL-17A, IL-17B, IL-17C, IL-17D, IL-17E (IL-25) and IL-17F. All IL-17 family members have four highly conserved cysteine residues that are involved in the formation of intrachain disulfide linkages and have two or more cysteine residues that may be involved in interchain disulfide linkages. Members of the IL-17 family have no sequence similarity to any other known cytokines.

Type-2 cytokines play an important role in mediating protective immunity to parasitic helminth infection, regulating effector functions such as B cell growth and IgE secretion, inducing goblet cell hyperplasia and associated mucus production, eosinophilia, mastocytosis and fibrosis. It is the central roles played by these cytokines in the regulation of these effector functions that have made them key therapeutic targets in asthma. Indeed, mouse models in which these cytokines are over-expressed show significant characteristics of asthma. Surprisingly then, efforts to ameliorate experimental asthma by blocking specific type-2 cytokines have, with the exception of inhibiting IL-13, proven unsuccessful.

Inhibition of IL-13 suppresses both AHR and airway inflammation although the mechanism remains unclear. However, given the complex pathophysiology and poorly understood etiology of asthma, it is uncertain whether targeting individual pathways will ultimately prove successful therapeutically.

Recently, over-expression of IL-25/IL-17E has been shown to induce type-2 responses in vivo and increase responsiveness to airway agonists. IL-25$^{-/-}$ mice failed to expel helminth parasites; a key indicator of an ineffectual type-2 response.

The present inventors have produced antibodies against IL-25 and identified an antibody molecule which binds with ultra-high affinity and specificity to IL-25. Two blocking antibodies out of the twenty-three screened were identified, with one having an extremely slow off-rate.

Binding Molecules

As used herein the term "binding molecule" refers to an intact immunoglobulin including monoclonal antibodies, polyclonal antibodies, chimeric antibodies, humanized or human antibodies, as well as antibodies fragments and functional variants including antigen-binding and/or variable domain comprising fragment of an immunoglobulin that competes with the intact immunoglobulin for specific binding to the binding partner of the immunoglobulin, e.g. IL-25.

In one aspect, the disclosed IL-25 binding molecules can comprise an anti-IL-25 antibody (for example, an anti-IL-25 antibody). The term "antibodies" is used herein in a broad sense and includes both polyclonal and monoclonal antibodies. As used herein, the term "antibody" encompasses, but is not limited to, whole immunoglobulin (i.e., an intact antibody) of any class. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with IL-25 such that IL-25 is inhibited from interacting with IL-17RA and/or IL-17RB. Antibodies that bind the disclosed regions of IL-25 involved in the interaction between IL-25 and IL-17RA and/or IL-17RB are also disclosed.

Native antibodies are usually heterotetrameric glycoproteins, composed of two identical light (L) chains and two identical heavy (H) chains. The disclosed IL-25 binding molecules whether monoclonal antibodies, polyclonal antibodies, chimeric antibodies, humanized or human antibodies, as well as antibodies fragments and functional variants can comprise all or a portion of light and heavy chains.

In a complete antibody, typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant (C(H)) domains. Each light chain has a variable domain at one end (V(L)) and a constant(C(L)) domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain domains of the heavy and light chains that differ in sequence among antibodies and are used in the binding and specificity of each particular antibody for its particular antigen. However, the variability is not usually evenly distributed through the variable domains of antibodies. The more highly conserved portions of the variable domains are called the framework (FR). The variable domains of native heavy and light chains each comprise four FR regions, largely adopting a n-sheet configuration, connected by three complementarity determining regions (CDRs), which form loops connecting, and in some cases forming part of, the β-sheet structure. The variability is typically concentrated in the CDRs or hypervariable regions both in the light chain and the heavy chain variable domains.

The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The term "complementary determining regions" as used herein means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically.

The constant domains are not involved directly in binding an antibody to an antigen, but exhibit various effector functions, such as participation of the antibody in antibody-dependent cellular toxicity.

In one aspect, disclosed herein are isolated IL-25 binding molecules comprising a heavy chain variable domain comprising one or more Complementary Determining Regions (CDR)s as set forth in SEQ ID NO: 1, SEQ ID NO: 2, SEQ ID NO: 3, SEQ ID NO: 7, SEQ ID NO: 8, and/or SEQ ID NO: 9. For example, disclosed herein are IL-25 binding molecules comprising a heavy chain variable domain comprising CDRs as set forth in SEQ ID NO: 1 and SEQ ID NO: 2; SEQ ID NO: 1 and SEQ ID NO: 3; SEQ ID NO: 2 and SEQ ID NO: 3; SEQ ID NO: 1, SEQ ID NO: 2, and SEQ ID NO: 3; SEQ ID NO: 7 and SEQ ID NO: 8; SEQ ID NO: 7 and SEQ ID NO: 9; SEQ ID NO: 8 and SEQ ID NO: 9; and SEQ ID NO: 7, SEQ ID NO: 8, and SEQ ID NO: 9. Also disclosed are IL-25 binding molecules comprising a heavy chain variable domain wherein the heavy chain variable domain comprises SEQ ID NO: 13 or SEQ ID NO 15.

It is understood and herein contemplated that the disclosed complimentary determining regions of the heavy chain variable domains in the disclosed IL-25 binding molecules can be contiguous or separated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. Thus, disclosed herein are IL-25 binding molecules comprising heavy chain variable domains comprising at least two CDRs wherein the first CDR is separated from the second CDR by 10, 11, 12, 13, 14, 15, 16, 17, 18, 19, or 20 amino acids. For example, disclosed herein are IL-25 binding molecules comprising at least two CDRs wherein the first CDR comprises SEQ ID NO: 1 or SEQ ID NO: 7, and the second CDR comprises SEQ ID NO: 2 or SEQ ID NO: 8, and wherein the first CDR and the second CDR are separated by 10, 11, 12, 13, 14, 15, 16, 17, 18, 19, or 20 amino acids. Also disclosed herein are IL-25 binding molecules comprising three CDRs wherein the first CDR comprises SEQ ID NO: 1 or SEQ ID NO: 7; the second CDR comprises SEQ ID NO: 2 or SEQ ID NO: 8; and the third CDR comprises SEQ ID NO: 3 or SEQ ID NO: 9; and wherein the second CDR and the third CDR are separated by 25, 26, 27, 28, 29, 30, 31, 32, 33, 34, 35, 36, 37, 38, 39, or 40 amino acids.

It is understood and herein contemplated that the IL-25 binding molecules can comprise a light chain variable domain instead of or in addition to a heavy chain variable domain. Thus, in one aspect, disclosed herein are IL-25 binding molecules comprising a light chain variable domain comprising one or more CDRs as set forth in SEQ ID NO: 4, SEQ ID NO: 5, SEQ ID NO: 6, SEQ ID NO: 10, SEQ ID NO: 11, and/or SEQ ID NO: 12. For example, disclosed herein are IL-25 binding molecules comprising a light chain variable domain comprising CDRs as set forth in SEQ ID NO: 4 and SEQ ID NO: 5; SEQ ID NO: 4 and SEQ ID NO: 6; SEQ ID NO: 5 and SEQ ID NO: 6; SEQ ID NO: 4, SEQ ID NO: 5, and SEQ ID NO: 6; SEQ ID NO: 10 and SEQ ID NO: 11; SEQ ID NO: 10 and SEQ ID NO: 12; SEQ ID NO: 11 and SEQ ID NO: 12; and SEQ ID NO: 10, SEQ ID NO: 11, and SEQ ID NO: 12. Also disclosed herein are isolated IL-25 binding molecules comprising a light chain variable domain wherein the light chain variable domain comprises SEQ ID NO: 14 or SEQ ID NO 16.

It is understood and herein contemplated that the disclosed complimentary determining regions of the light chain variable domains in the disclosed IL-25 binding molecules can be contiguous or separated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. Thus, disclosed herein are IL-25 binding molecules comprising light chain variable domains comprising a light chain variable domain wherein the light chain variable domain comprises at least two CDRs wherein the first CDR is separated from the second CDR by 10, 11, 12, 13, 14, 15, 16, 17, 18, 19, or 20 amino acids. For example, disclosed herein are IL-25 binding molecules comprising at least two CDRs wherein the first CDR comprises SEQ ID NO: 4, SEQ ID NO: 10, SEQ ID NO: 16, or SEQ ID NO: 22 and the second CDR comprises SEQ ID NO: 5, SEQ ID NO: 11, SEQ ID NO: 17, or SEQ ID NO: 23, and wherein the first CDR and the second CDR are separated by 10, 11, 12, 13, 14, 15, 16, 17, 18, 19, or 20 amino acids. Also disclosed herein are IL-25 binding molecules comprising a light chain variable domain wherein the light chain variable domain comprises three CDRs wherein the first CDR comprises SEQ ID NO: 4 or SEQ ID NO: 10; the second CDR comprises SEQ ID NO: 5 or SEQ ID NO: 11; and the third CDR comprises SEQ ID NO: 6 or SEQ ID NO: 12; and wherein the second CDR and the third CDR are separated by 25, 26, 27, 28, 29, 30, 31, 32, 33, 34, 35, 36, 37, 38, 39, or 40 amino acids.

In one aspect, it is understood and herein contemplated that the disclosed IL-25 binding molecules can comprise both a heavy chain variable domain and a light chain variable domain. It is further understood that said IL-25 binding molecules can comprise any one, two, or three of the heavy chain variable domain CDRs in combination with any one, two, or three of the light chain variable domain CDRs disclosed herein. Accordingly, the IL-25 binding molecule can comprise one, two, or three of the heavy chain variable domains CDRs selected from the group comprising SEQ ID NO: 1, SEQ ID NO: 2, SEQ ID NO: 3, SEQ ID NO: 7, SEQ ID NO: 8, and/or SEQ ID NO: 9, and one, two, or three of the light chain variable domains CDRs selected from the group comprising SEQ ID NO: 4, SEQ ID NO: 5, SEQ ID NO: 6, SEQ ID NO: 10, SEQ ID NO: 11 and/or SEQ ID NO: 12. For example, disclosed herein are IL-25 binding molecules comprising a heavy chain variable domain wherein the heavy chain variable domain comprises SEQ ID NO: 13 or SEQ ID NO 15, and a light chain variable domain wherein the light chain variable domain comprises SEQ ID NO: 14 or SEQ ID NO 16.

Accordingly, in one embodiment is an IL-25 binding molecule designated ABM109 which comprises an antigen binding site comprising at least one immunoglobulin heavy chain variable domain ($V_H$) which comprises in sequence hypervariable regions CDR1, CDR2 and CDR3, said CDR1 having the amino acid sequence SEQ ID NO: 1 (SYWIE), said CDR2 having the amino acid sequence SEQ ID NO: 2 (QILPGIGSTNYNEKFKG), and said CDR3 having the amino acid sequence SEQ ID NO: 3 (GYGNYGDY); or direct CDR equivalents thereof. In one aspect, the IL-25 binding molecule (such as, for example ABM109) can also comprise at least one immunoglobulin light chain variable domain ($V_L$) which comprises in sequence hypervariable regions CDR1', CDR2' and CDR3', said CDR1' having the amino acid sequence SEQ ID NO: 4 (RASESVDSYG-NSFM), said CDR2' having the amino acid sequence SEQ ID NO: 5 (RASNLES) and said CDR3' having the amino acid sequence SEQ ID NO: 6 (QQSNEDPLT) or direct CDR' equivalents thereof.

In one aspect, also disclosed is an IL-25 binding molecule designated ABM125 which comprises an antigen binding site comprising at least one immunoglobulin heavy chain variable domain ($V_H$) which comprises in sequence hypervariable regions CDR1, CDR2 and CDR3, said CDR1 having the amino acid sequence SEQ ID NO: 7 (TSGMGVG), said CDR2 having the amino acid sequence SEQ ID NO: 8 (HIWWDDVKRYNPALKS), and said CDR3 having the amino acid sequence SEQ ID NO: 9 (TLPHFFDY); or direct CDR equivalents thereof. In one aspect, the IL-25 binding molecule (such as, for example ABM125) can also comprise at least one immunoglobulin light chain variable domain ($V_L$) which comprises in sequence hypervariable regions CDR1', CDR2' and CDR3', said CDR1' having the amino acid sequence SEQ ID NO: 10 (SASSSVSYMY), said CDR2' having the amino acid sequence SEQ ID NO: 11 (RTSNLAS) and said CDR3' having the amino acid sequence SEQ ID NO: 12 (KQYHSYPPTWT) or direct CDR' equivalents thereof.

As noted above the disclosed IL-25 binding molecules can also be fragments of antibodies. As used herein, the term "antibody or fragments thereof" encompasses chimeric antibodies and hybrid antibodies, with dual or multiple antigen or epitope specificities, and fragments, such as F(ab')2, Fab', Fab, Fv, sFv, dAb, complementarity determining region (CDR) fragments, single-chain antibodies (scFv), bivalent single-chain antibodies, diabodies, triabodies, tetrabodies, (poly)peptides that contain at least a fragment of an immunoglobulin that is sufficient to confer specific antigen binding to the (poly)peptide, etc., including hybrid fragments. Thus, fragments of the antibodies that retain the ability to bind their specific antigens are provided. For example, fragments of antibodies which maintain IL-25 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or fragments thereof" are conjugates of antibody fragments and antigen binding proteins (single chain antibodies). Conjugated antibodies or fragments refer to antibodies or fragments that are operatively linked or otherwise physically or functionally associated with an effector moiety or tag, such as inter alia a toxic substance, a radioactive substance, fluorescent substance, a liposome, or an enzyme as described, for example, in U.S. Pat. No. 4,704,692, the contents of which are hereby incorporated by reference.

Regardless of structure, the antigen-binding fragments disclosed herein can bind with the same antigen that is recognized by the intact immunoglobulin. An antigen-binding fragment can comprise a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

The term "functional variant", as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g. IL-25 (including IL-25), with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e. the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

As disclosed herein, the binding molecules, antibodies, fragments, and variants are able to specifically bind to an antigenic target, such as, for example, IL-25. The term "specifically binding", as used herein, in reference to the interaction of a binding molecule, e.g. an antibody, and its binding partner, e.g. an antigen, means that the interaction is dependent upon the presence of a particular structure, e.g. an antigenic determinant or epitope, on the binding partner. In other words, the antibody preferentially binds or recognizes the binding partner even when the binding partner is present in a mixture of other molecules. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIAcore, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

In one aspect, the disclosed antibodies or binding molecules disclosed herein can be human antibodies or human binding molecules. The term "human", when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semisynthetic molecules based on human sequences are also considered to be human as used herein.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, FAT framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature*, 321:522-525 (1986); Riechmann et al., *Nature*, 332:323-327 (1988); and Presta, *Curr. Op. Struct. Biol.*, 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.*, 151:2296 (1993) and Chothia et al., *J. Mol Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

In some aspect, it can be important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 March 1994).

In one specific aspect, a humanized version of ABM109, designated ABM109.2, contains the ABM109 heavy and light chain CDRs and retains specific binding and neutralization of human, mouse and simian IL-25. The heavy and light chain variable regions are listed in SEQ ID NO:17 and SEQ ID NO:18, respectively.

Disclosed are hybridoma cells that produces the monoclonal antibody. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA*, 81:6851-6855 (1984)).

Monoclonal antibodies may be prepared using hybridoma methods, such as those described by Kohler and Milstein, *Nature*, 256:495 (1975) or Harlow and Lane. *Antibodies, A Laboratory Manual*. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises IL-25. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of IL-25 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma*. 1998 December; 17(6):569-76; Kilpatrick K E et al. High-affinity monoclonal antibodies to PED/PEA-15 generated using 5 μg of DNA. *Hybridoma*. 2000 August; 19(4):297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of an anti-IL-25 antibody as fusion proteins. The antigen is produced by inserting a gene fragment in-frame between the signal sequence and the mature protein domain of the anti-IL-25 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.,* 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against IL-25. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane *Antibodies, A Laboratory Manual* Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The term "isolated", when applied to binding molecules as defined herein, refers to binding molecules that are substantially free of other proteins or polypeptides, particularly free of other binding molecules having different antigenic specificities, and are also substantially free of other cellular or tissue material and/or chemical precursors or other chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. Preferably, substantially free means that the binding molecule will typically comprise about 50%, 60%, 70%, 80% or 90% W/W of a sample, more usually about 95%, and preferably will be over 99% pure.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for IL-25 (including IL-25) and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, *Antibodies, A Laboratory Manual*, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

Alternatively, the disclosed antibodies can be made utilizing transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA*, 90:2551-255 (1993); Jakobovits et al., *Nature*, 362:255-258 (1993); Bruggemann et al., Year in Immuno., 7:33 (1993)). Human antibodies can also be produced in phage display libraries (Hoogenboom et al., *J. Mol. Biol.*, 227:381 (1991); Marks et al., *J. Mol. Biol.*, 222:581 (1991)). The techniques of Cote et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immuno.*, 147(1):86-95 (1991)).

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant Ga. (1992) *Synthetic Peptides: A User Guide*. W.H. Freeman and Co., N.Y. (1992); Bodansky M and Trost B., Ed. (1993) *Principles of Peptide Synthesis*. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science*, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) *FEBS Lett.* 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with IL-25. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., *Anal. Biochem.*, 107:220 (1980).

Also provided is an antibody reagent kit comprising containers of the monoclonal antibody or fragment thereof and one or more reagents for detecting binding of the anti-IL-25 antibody or fragment thereof to the IL-25 molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

As stated throughout, in one aspect disclosed herein are isolated IL-25 binding molecules comprising a heavy chain variable domain comprising one or more CDRs as set forth in SEQ ID NO: 1, SEQ ID NO: 2, and/or SEQ ID NO: 3.

Also disclosed are IL-25 binding molecules of any preceding aspect, wherein the CDR is SEQ I NO: 1, SEQ I NO: 2, and/or SEQ I NO: 3.

In one aspect, disclosed herein are isolated IL-25 binding molecules of any preceding aspect, wherein the heavy chain variable domain comprises SEQ ID NO: 1 and SEQ ID NO: 2; SEQ ID NO: 1 and SEQ ID NO: 3; SEQ ID NO: 2 and SEQ ID NO: 3; and/or SEQ ID NO: 1, SEQ ID NO: 2, and SEQ ID NO: 3.

In one aspect, disclosed herein are isolated IL-25 binding molecules of any preceding aspect, wherein SEQ ID NO: 1 and SEQ ID NO: 2 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 2 and SEQ ID NO: 3 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the heavy chain variable domain comprises SEQ ID NO: 13.

In one aspect, disclosed herein are isolated IL-25 binding molecules of any preceding aspect, further comprising a light chain variable domain comprising one or more CDRs as set forth in SEQ ID NO: 4, SEQ ID NO: 5, and SEQ ID NO: 6.

In one aspect, disclosed herein are isolated IL-25 binding molecules of any preceding aspect, wherein the light chain variable domain comprises SEQ ID NO: 4 and SEQ ID NO: 5; SEQ ID NO: 4 and SEQ ID NO: 6; SEQ ID NO: 5 and SEQ ID NO: 6; and/or SEQ ID NO: 4, SEQ ID NO: 5, and SEQ ID NO: 6.

In one aspect, disclosed herein are isolated IL-25 binding molecules of any preceding aspect, wherein SEQ ID NO: 4 and SEQ ID NO: 5 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 5 and SEQ ID NO: 6 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the light chain variable domain comprises SEQ ID NO: 14.

In one aspect, disclosed herein are isolated IL-25 binding molecules of any preceding aspect comprising a heavy chain variable domain and light chain variable domain, wherein the heavy chain variable domain comprises SEQ ID NO: 13 and the light chain variable domain comprises SEQ ID NO: 14.

In one aspect, disclosed herein are isolated IL-25 binding molecules comprising a light chain variable domain comprising one or more CDRs as set forth in SEQ ID NO: 4, SEQ ID NO: 5, and SEQ ID NO: 6.

In one aspect, disclosed herein are isolated IL-25 binding molecules of any preceding aspect, wherein the light chain variable domain comprises SEQ ID NO: 4 and SEQ ID NO: 5; SEQ ID NO: 4 and SEQ ID NO: 6; SEQ ID NO: 5 and SEQ ID NO: 6; and/or SEQ ID NO: 4, SEQ ID NO: 5, and SEQ ID NO: 6.

In one aspect, disclosed herein are isolated IL-25 binding molecules of any preceding aspect, wherein SEQ ID NO: 4 and SEQ ID NO: 5 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 5 and SEQ ID NO: 6 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the light chain variable domain comprises SEQ ID NO: 14.

In one aspect, disclosed herein are isolated IL-25 binding molecules comprising a heavy chain variable domain comprising one or more CDRs as set forth in SEQ ID NO: 7, SEQ ID NO: 8, and SEQ ID NO: 9.

In one aspect, disclosed herein are isolated IL-25 binding molecules of any preceding aspect, wherein the heavy chain variable domain comprises SEQ ID NO: 7 and SEQ ID NO:

8; SEQ ID NO: 7 and SEQ ID NO: 9; SEQ ID NO: 8 and SEQ ID NO: 9; and/or SEQ ID NO: 7, SEQ ID NO: 8, and SEQ ID NO: 9.

In one aspect, disclosed herein are isolated IL-25 binding molecules of any preceding aspect, wherein SEQ ID NO: 7 and SEQ ID NO: 8 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 8 and SEQ ID NO: 9 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the heavy chain variable domain comprises SEQ ID NO: 15.

In one aspect, disclosed herein are isolated IL-25 binding molecules of any preceding aspect, further comprising a light chain variable domain comprising one or more CDRs as set forth in SEQ ID NO: 10, SEQ ID NO: 11, and SEQ ID NO: 12.

In one aspect, disclosed herein are isolated IL-25 binding molecules of any preceding aspect, wherein the light chain variable domain comprises SEQ ID NO: 10 and SEQ ID NO: 11; SEQ ID NO: 10 and SEQ ID NO: 12; SEQ ID NO: 11 and SEQ ID NO: 12; and/or SEQ ID NO: 10, SEQ ID NO: 11 and SEQ ID NO: 12.

In one aspect, disclosed herein are isolated IL-25 binding molecules of any preceding aspect, wherein SEQ ID NO: 10 and SEQ ID NO: 11 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 11 and SEQ ID NO: 12 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the light chain variable domain comprises SEQ ID NO: 16.

In one aspect, disclosed herein are isolated IL-25 binding molecules of any preceding aspect comprising a heavy chain variable domain and light chain variable domain, wherein the heavy chain variable domain comprises SEQ ID NO: 15 and the light chain variable domain comprises SEQ ID NO: 16.

In one aspect, disclosed herein are isolated IL-25 binding molecules comprising a light chain variable domain comprising one or more CDRs as set forth in SEQ ID NO: 10, SEQ ID NO: 11 and SEQ ID NO: 12.

In one aspect, disclosed herein are isolated IL-25 binding molecules of any preceding aspect, wherein the light chain variable domain comprises SEQ ID NO: 10 and SEQ ID NO: 11; SEQ ID NO: 10 and SEQ ID NO: 12; SEQ ID NO: 11 and SEQ ID NO: 12; and/or SEQ ID NO: 10, SEQ ID NO: 11 and SEQ ID NO: 12.

In one aspect, disclosed herein are isolated IL-25 binding molecules of any preceding aspect, wherein SEQ ID NO: 10 and SEQ ID NO: 11 are separated by 10, 11, 12, 13, 14, 15, 16, 17, 18, 19, or 20 amino acids.

In one aspect, disclosed herein are isolated IL-25 binding molecules of any preceding aspect, wherein SEQ ID NO: 11 and SEQ ID NO: 12 are separated by 25, 26, 27, 28, 29, 30, 31, 32, 33, 34, 35, 36, 37, 38, 39, or 40 amino acids.

In one aspect, disclosed herein are isolated IL-25 binding molecules of any preceding aspect, wherein the light chain variable domain comprises SEQ ID NO: 16.

In one aspect, disclosed herein are isolated IL-25 binding molecules of any preceding aspect, wherein the heavy chain variable domain comprises SEQ ID NO: 17.

In one aspect, disclosed herein are isolated IL-25 binding molecules of any preceding aspect, wherein the light chain variable domain comprises SEQ ID NO: 18.

In one aspect, disclosed herein are method of treating, preventing, and/or inhibiting a rhinoviral infection, airway inflammation, rheumatoid arthritis, osteoarthritis, bone erosion, intraperitoneal abscesses and adhesions, inflammatory bowel disorder, allograft rejection, psoriasis, certain types of cancer, angiogenesis, atherosclerosis, cystic fibrosis and multiple sclerosis comprising administering a therapeutic amount of any of the IL-25 binding molecules of any preceding aspect.

1. Homology/Identity

It is understood that one way to define any known variants and derivatives or those that might arise, of the disclosed genes and proteins herein is through defining the variants and derivatives in terms of homology to specific known sequences. For example, SEQ ID NO: 13 sets forth a particular sequence of an IL-25 heavy chain variable domain. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Peptides a) Protein Variants

As discussed herein there are numerous variants of the IL-25 binding molecules and IL-25 binding CDRs and heavy and light chain variable regions disclosed herein that are known and herein contemplated. In addition, to the known functional strain variants there are derivatives of the IL-25 binding molecules and IL-25 binding CDRs and heavy and light chain variable regions which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. As used herein, "insertions" refer to a change in an amino acid or nucleotide sequence resulting in the addition of one or more amino acid or nucleotide residues, respectively, as compared to the parent, often the naturally occurring, molecule. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative Substitutions, others are known in the art.

| Ala | Ser |
|---|---|
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NOs: 13, 14, 15 and 16. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. In addition, for example, a disclosed conservative derivative of SEQ ID NOs: 1, 2, 3, 4, 5, 6, 7, 8, 9, 10, 11, 12, 13, 14, 15, 16, 17 or 18 such as the substitution of an isoleucine (I) at for a valine (V). It is understood that for this mutation all of the nucleic acid sequences that encode this particular derivative of the SEQ ID NOs:1, 2, 3, 4, 5, 6, 7, 8, 9, 10, 11, 12, 13, 14, 15, 16, 17 or 18 are also disclosed.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$—(These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) (—$CH_2NH$—, $CH_2CH_2$—); Spatola et al. *Life Sci* 38:1243-1249 (1986) (—$CH\ H_2$—S); Hann *J. Chem. Soc Perkin Trans.* I 307-314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appin, EP 45665 CA (1982): 97:39405 (1982) (—CH(OH) $CH_2$—); Holladay et al. *Tetrahedron. Lett* 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

In one aspect, the disclosed IL-25 binding molecules may further comprise a label. As used herein, a label can include a fluorescent dye, a member of a binding pair, such as biotin/streptavidin, a metal (e.g., gold), radioactive substituent, or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs-AutoFluorescent Protein-(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzimide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson; Calcium Green; Calcium Green-1 Ca$^{2+}$ Dye; Calcium Green-2 Ca$^{2+}$; Calcium Green-5N Ca$^{2+}$; Calcium Green-C18 Ca$^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; FluoroEmerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin EBG; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine B B; Rhodamine B G; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

3. Pharmaceutical Carriers/Delivery of Pharmaceutical Products

As described above, the compositions can also be administered in vivo in a pharmaceutically acceptable carrier (also referred to herein as a pharmaceutically acceptable excipient). By "pharmaceutically acceptable" is meant a material that is not biologically or otherwise inert, i.e., the material may be administered to a subject, along with the nucleic acid or vector, without causing any undesirable biological effects or interacting in a deleterious manner with any of the other components of the pharmaceutical composition in which it is contained.

The carrier would naturally be selected to minimize any degradation of the active ingredient and to minimize any adverse side effects in the subject, as would be well known to one of skill in the art. Thus, in one aspect, disclosed herein are pharmaceutical compositions comprising any of the IL-25 binding molecules disclosed herein.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, Immunolog. Reviews, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

4. Therapeutic Uses and Methods

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

In one aspect, it is understood and herein contemplated that the disclosed IL-25 binding molecules can be used to treat, prevent, or inhibit an inflammatory condition or disease, such as, for example, rhinoviral infection, airway inflammation, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS"). Thus, in one aspect, disclosed herein are methods of treating, preventing, or inhibiting a rhinoviral infection, airway inflammation, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") comprising administering any of the IL-25 binding molecules disclosed herein. For example, disclosed herein are method of treating, preventing, or inhibiting a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") comprising administering to a subject one, two, three, or more IL-25 binding molecules comprising a heavy chain variable domain comprising one or more Complementary Determining Regions (CDR)s as set forth in SEQ ID NO: 1, SEQ ID NO: 2, SEQ ID NO: 3, SEQ ID NO: 7, SEQ ID NO: 8, and SEQ ID NO: 9. For example, disclosed herein are methods of treating, inhibiting, or preventing a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") comprising administering to a subject one or more IL-25 binding molecules comprising a heavy chain variable domain comprising CDRs as set forth in SEQ ID NO: 1 and SEQ ID NO: 2; SEQ ID NO: 1 and SEQ ID NO: 3; SEQ ID NO: 2 and SEQ ID NO: 3; SEQ ID NO: 1, SEQ ID NO: 2, and SEQ ID NO: 3; SEQ ID NO: 7 and SEQ ID NO: 8; SEQ ID NO: 7 and SEQ ID NO: 9; SEQ ID NO: 8 and SEQ ID NO: 9; and/or SEQ ID NO: 7, SEQ ID NO: 8, and SEQ ID NO: 9; In one aspect, the disclosed treatment, prevention, or inhibition methods can comprise administering to a subject IL-25 binding molecules comprising a heavy chain variable domain wherein the heavy chain variable domain comprises SEQ ID NO: 13 or SEQ ID NO 27.

It is also understood and herein contemplated that the disclosed methods of treating, preventing, or inhibiting a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") can comprise administering to a subject with said condition or disease an IL-25 binding molecules comprising a light chain variable domain instead of or in addition to a heavy chain variable domain. In one aspect, disclosed herein are method of treating, preventing, or inhibiting a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") in a subject comprising administering to the subject one, two, three, or more IL-25 binding molecule comprising a light chain variable domain comprising one or more CDRs as set forth in SEQ ID NO: 4, SEQ ID NO: 5, SEQ ID NO: 6, SEQ ID NO: 10, SEQ ID NO: 11, and/or SEQ ID NO: 12. For example, disclosed herein are treatment, prevention, or inhibition methods comprising administering to a subject one or more of the IL-25 binding molecules comprising a light chain variable domain comprising CDRs as set forth in SEQ ID NO: 4 and SEQ ID NO: 5; SEQ ID NO: 4 and SEQ ID NO: 6; SEQ ID NO: 5 and SEQ ID NO: 6; SEQ ID NO: 4, SEQ ID NO: 5, and SEQ ID NO: 6; SEQ ID NO: 10 and SEQ ID NO: 11; SEQ ID NO: 10 and SEQ ID NO: 12; SEQ ID NO: 11 and SEQ ID NO: 12; and/or SEQ ID NO: 10, SEQ ID NO: 11, and SEQ ID NO: 12. Also disclosed herein are methods wherein the IL-25 binding molecules comprises a light chain variable domain wherein the light chain variable domain comprises SEQ ID NO: 14 or SEQ ID NO 16.

In one aspect, it is understood and herein contemplated that the disclosed IL-25 binding molecules for use in the disclosed treatment, prevention, and/or inhibition methods can comprise both a heavy chain variable domain and a light chain variable domain. It is further understood that said IL-25 binding molecules used in said methods of treatment, prevention, and/or inhibition can comprise any one, two, or three of the heavy chain variable domain CDRs in combination with any one, two, or three of the light chain variable domain CDRs disclosed herein. Accordingly, the IL-25 binding molecule for use in the disclosed methods of treating, preventing, or inhibiting a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") can comprise one, two, or three of the heavy chain variable domains CDRs selected from the group comprising SEQ ID NO: 1, SEQ ID NO: 2, SEQ ID NO: 3, SEQ ID NO: 7, SEQ ID NO: 8, and/or SEQ ID NO: 9, and one, two, or three of the light chain variable domains CDRs selected from the group comprising SEQ ID NO: 4, SEQ ID NO: 5, SEQ ID NO: 6, SEQ ID NO: 10, SEQ ID NO: 11 and/or SEQ ID NO: 12. For example, disclosed herein are methods of treating a subject with an a rhinoviral infection, airway inflammation, asthma, cystic fibrosis, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") comprising administering to the subject an IL-25 binding molecules comprising a heavy chain variable domain; wherein the heavy chain variable domain comprises SEQ ID NO: 13, SEQ ID NO 15 and/or SEQ ID NO 17; and a light chain variable domain; wherein the light chain variable domain comprises SEQ ID NO: 14, SEQ ID NO 16, and/or SEQ ID NO 18.

As used herein the terms "treatment," "treat," or "treating" refers to a method of reducing one or more of the effects of a disease or condition (such as, for example an inflammatory condition or a cancer) in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an inflammatory condition or cancer is considered to be a treatment if there is a 10% reduction in one or more symptoms of the condition or cancer in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the condition or disease or symptoms of the condition or disease. It is understood and herein contemplated that treatments as discussed herein can be prophylactic or therapeutic. Accordingly, in one aspect are methods of treating or reducing the severity of an inflammatory disease or condition in a subject comprising administering to the subject an IL-25 binding molecule. Also disclosed are methods of preventing or reducing the onset of an inflammatory disease or condition in a subject comprising administering to the subject an IL-25 binding molecule.

As used herein, the terms prevent, preventing, and prevention of an infection, refers to an action, for example, administration of a therapeutic agent (e.g., a composition disclosed herein), that occurs before or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%, 20%, 30%, 40%, 50%, 60%, 70%, 80%, 90% or greater relative to a control level. For example, the disclosed methods are considered to be a prevention if there is about a 10% reduction in onset, exacerbation or recurrence of inflammatory condition or a disease, or symptoms of an inflammatory condition or a disease in a subject when compared to control subjects that did not receive an IL-25 binding molecule for decreasing the inflammatory condition or disease.

It is understood and herein contemplated that the treatment, prevention, and inhibition methods disclosed herein contemplate both therapeutic and prophylactic applications of the IL-25 binding molecules disclosed herein.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Transgenic mice overexpressing mouse Ig-Alpha, mouse Ig-Beta and human interleukin 6 were injected intraperitoneally with recombinant human IL-25 (R&D Systems) at 2 week intervals. After a significant immune response was mounted as measured by serum ELISA, the lymph nodes, spleens and bone marrow cells were harvested, B cells surface-expressing IgM isotype antibodies were subtracted with magnetic beads, and the remaining cells were sorted for their ability to bind IL-25, using a MoFlo Fluorescence—Activated Cell Sorter (FIG. 1).

Figure 2:
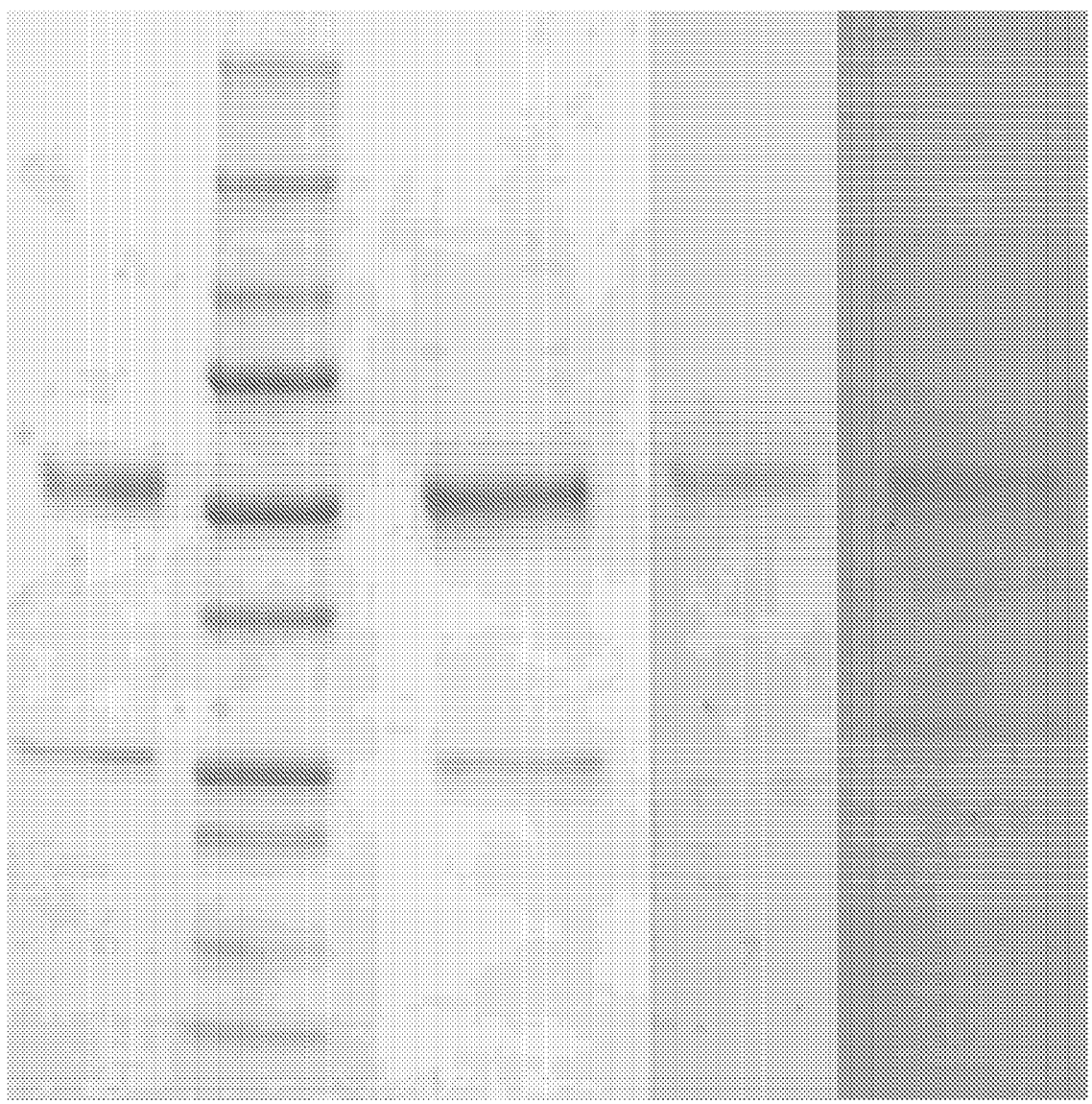
FIG. 2 shows denatured gel electrophoresis of antibodies: Lane 1: a human IgG4 positive control, Lane 2: Kaleidoscope pre-stained standard protein marker, Lane 3: ABM109, Lane 4: ABM125, Lane 5: ABM109.2.
Figure 3:
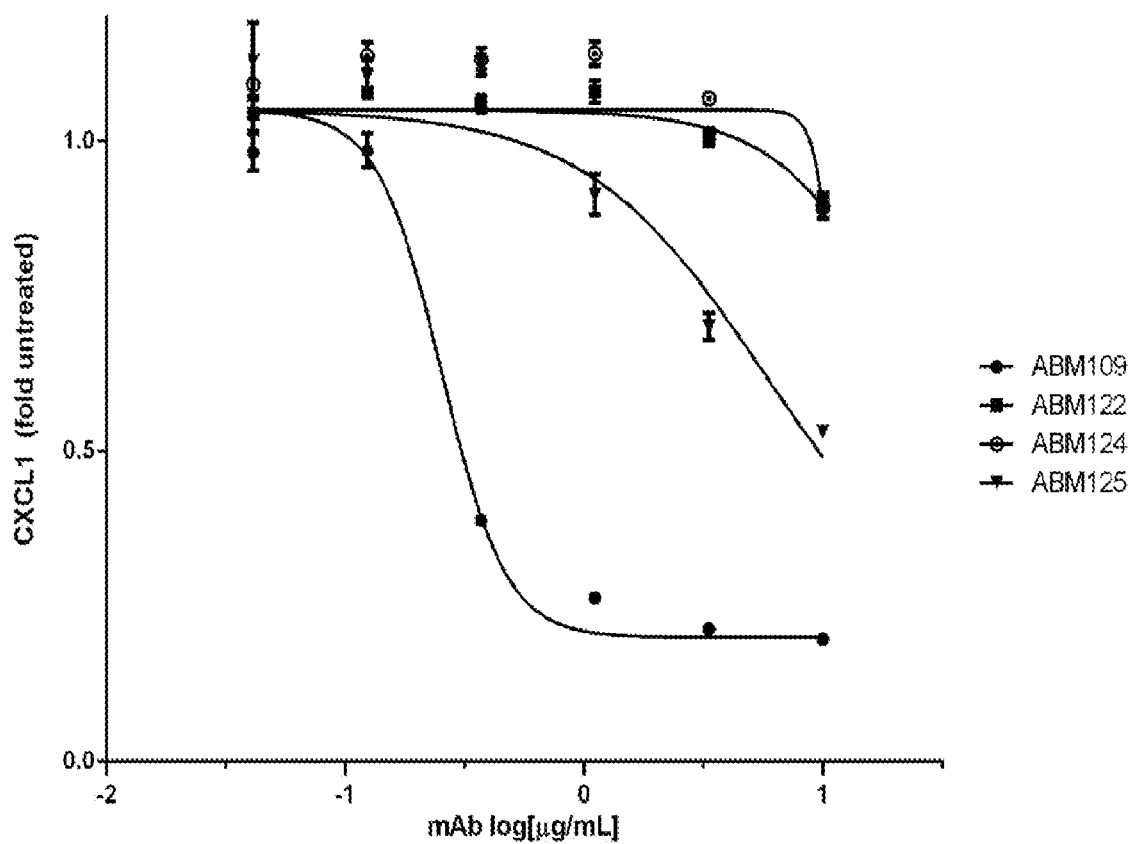
FIG. 3 shows a HT-29 cellular potency assay of monoclonal antibodies against IL-25.
Figures 4, 5:
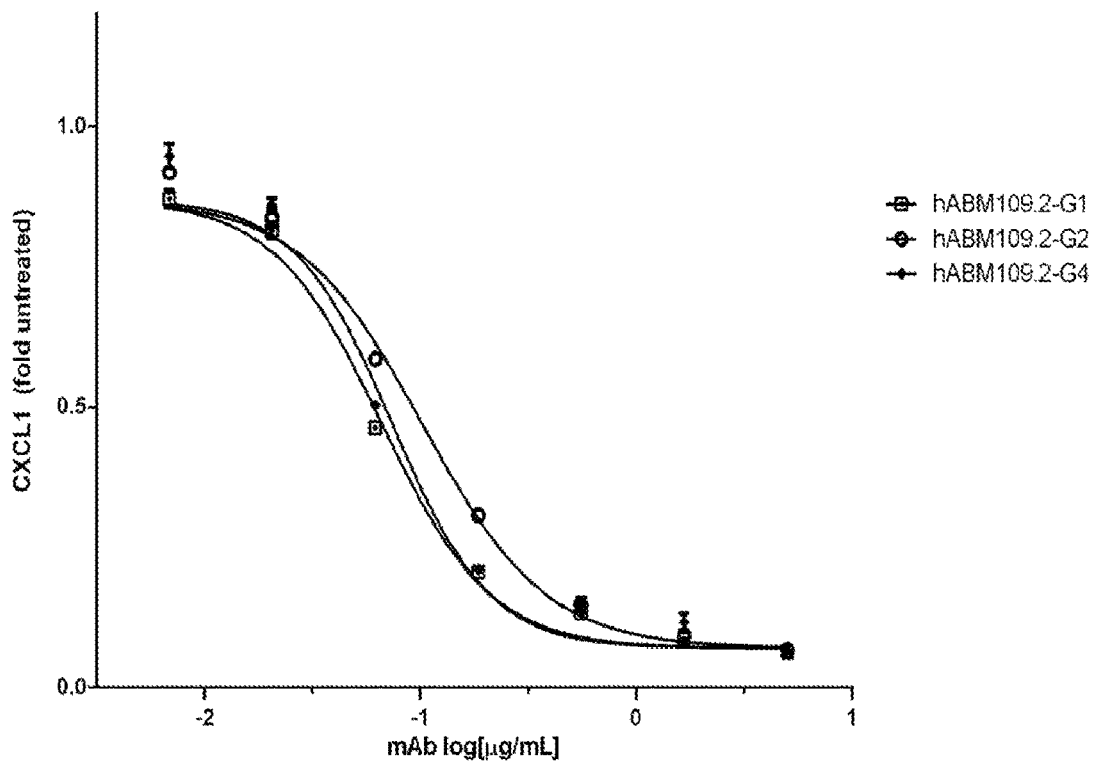
FIG. 4 shows HT-29 cellular potency assay of humanized monoclonal antibody ABM109.2 in IgG1, IgG2 and IgG4 isotypes.
FIG. 5 shows the surface plasmon resonance (SPR) of anti-IL25 monoclonal antibodies and calculated affinity of the antibodies.
Figure 6:
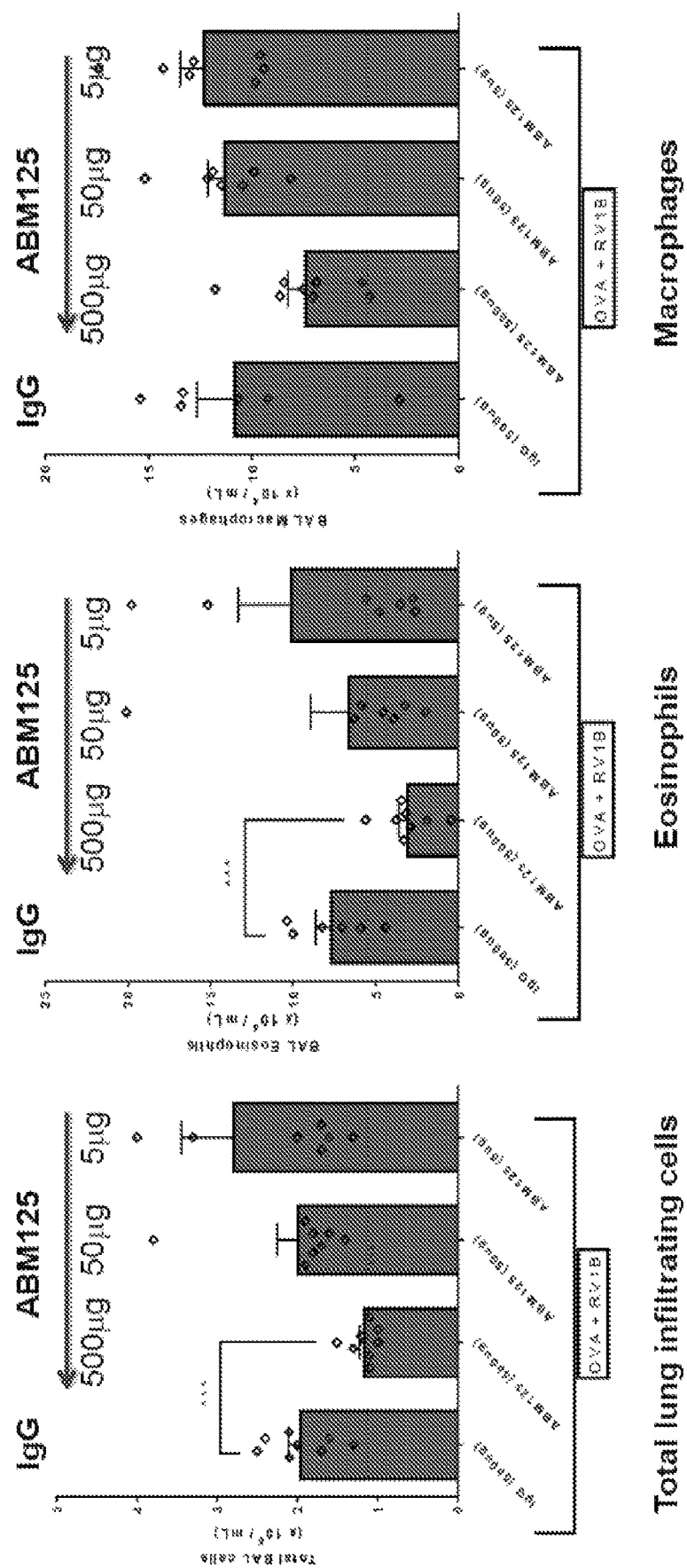
FIG. 6 shows the effects of ABM125 or control antibody (IgG) administration on total lung infiltrating cells, eosinophils and macrophages in a model of rhinovirus infection on allergic asthma in mice
Figure 7:
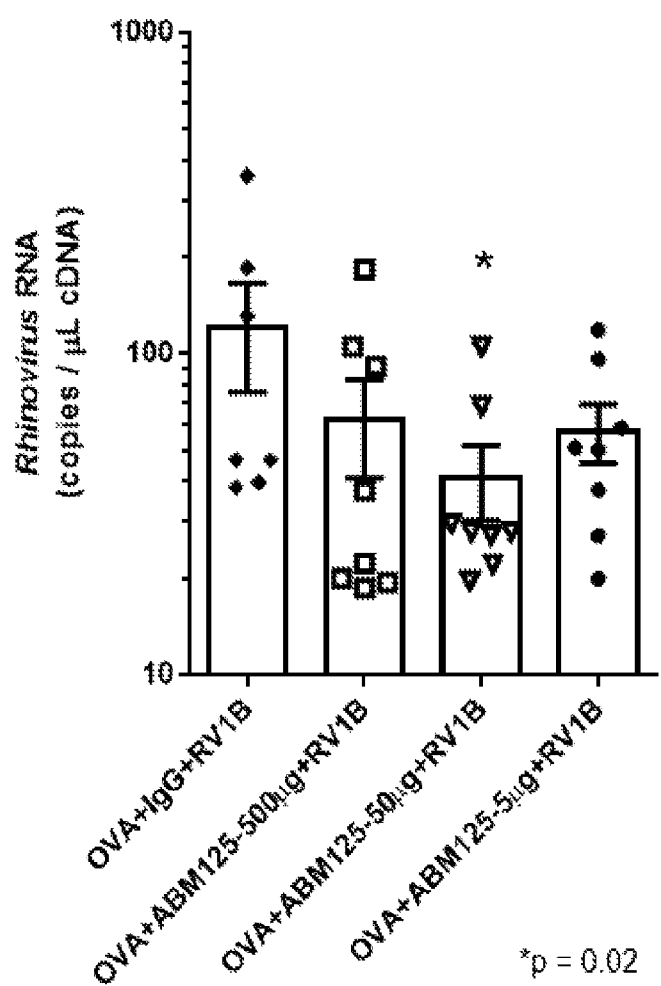
FIG. 7 shows the amount of detectable rhinovirus RNA in the lungs of mice treated with control antibody (IgG) or ABM125.
Figure 8:
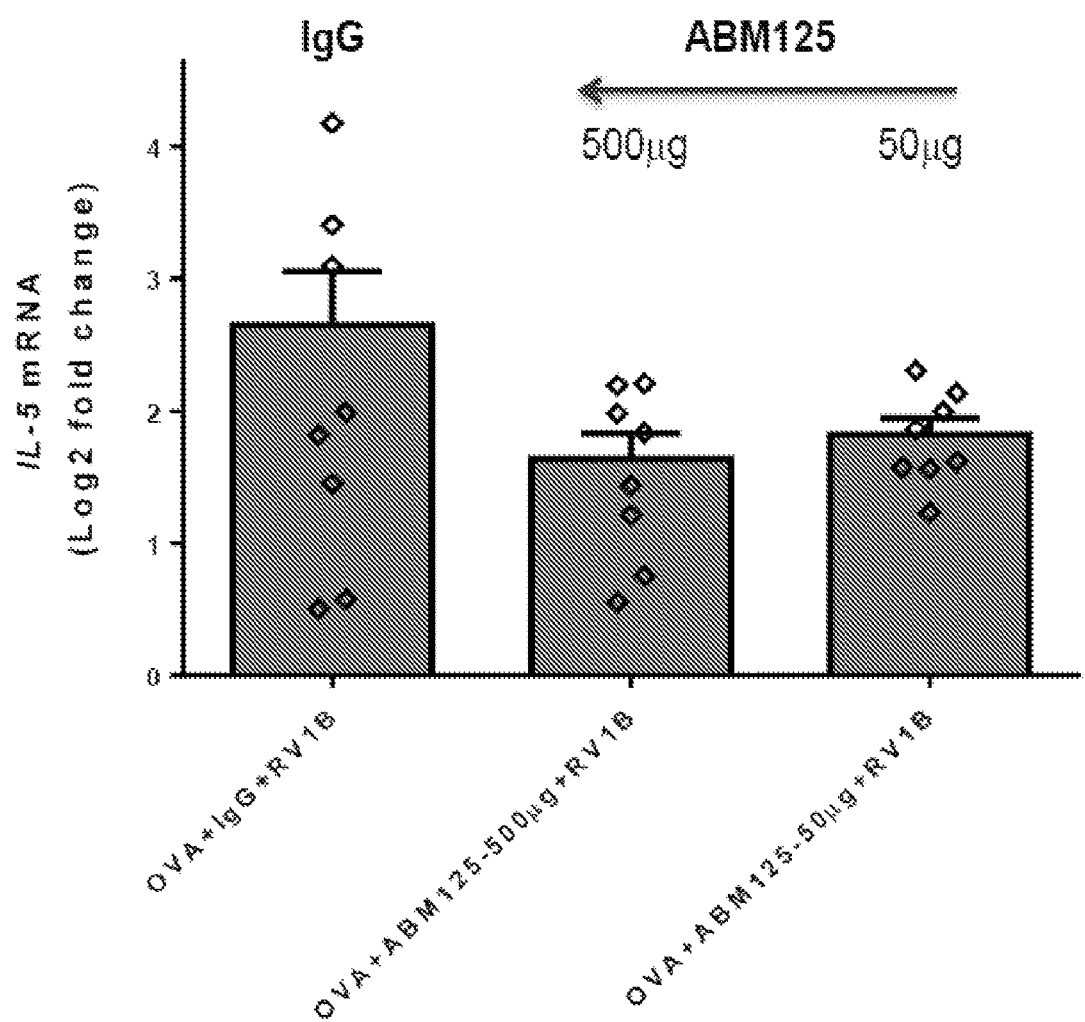
FIG. 8 shows the amount of detectable IL-5 RNA in the lungs of mice treated with control antibody (IgG) or ABM125.

Cells positive for IL-25 binding were sorted into 96-well plates, subjected to single cell RT-PCR to amplify variable regions, and the variable regions were cloned into expression vectors containing either a heavy chain human IgG4 constant region or light chain human IgK constant region. The resulting heavy and light chain clone pairs were transfected into HEK293 cells, and the resulting antibody protein was purified with protein A resin (FIG. 2) and assayed for its ability to neutralize recombinant human IL-25 activity in HT-29 cells (FIG. 3). A humanized version of ABM109 (designated ABM109.2) was also tested for potency in the HT-29 assay (FIG. 4).

The affinity of the antibodies for IL-25 were measured using Surface Plasma Resonance (SPR) using a Biacore T-100 (GE Healthcare). (FIG. 5, FIG. 9) Antibodies were immobilized to carboxymethylated dextran on flow cells 2-4 on CM5 chip (flow cell 1 used as a reference). rhIL25 or rmIL15 in HBS-P buffer was run over chip at increasing concentrations (2.5, 5.0, 10, 20, and 40 nM) with a 120 sec injection time for each concentration. After the 5$^{th}$ injection, HBS-P buffer was run through each flow cell and IL-25 was allowed to dissociate for 20 minutes. The surface was regenerated with a 30 second exposure of 10 mM Glycine-HCL pH 1.5. Single cycle kinetic analysis was performed on each antibody with the reference cell subtracted.

ABM125 was purified and administered to mice in a model of rhinovirus infection in allergic asthma. Mice were sensitized with low LPS hen egg ovalbumin (OVA 50 μg in 2 mg alum). Mice were then challenged with 50 μg ovalbumin (OVA) intranasally (i.n.) on three consecutive days. Directly after the final OVA challenge mice were administered intraperitoneally (i.p.) ABM125 or isotype control (IgG). Four hours after mAb dosing mice were infected i.n. with 2.5×10$^6$ TCID$_{50}$ RV1B. Inflammatory responses were assessed at day three post injection. Cellular recruitment was then assessed in bronchoalveolar lavage fluid and lung mRNA expression of IL-5 was assessed by qPCR with SYBR Green chemistry, expressed at Log 2 (fold change) relative to Saline/PBS controls at 3 days post-infection.

Total RNA was extracted from mouse apical lung lobes stored in RNA later (Qiagen), followed by cDNA synthesis (OMNISCRIPT® RT kit, Qiagen). RV-1B genomic RNA primers and probe sequences: sense 5'-GT-GAAGAGCCSCRTGTGCT-3' (SEQ ID NO: 19) 50 nm, antisense 5'-GCTSCAGGGTTAAGGTTAGCC-3' (SEQ ID NO: 20) 300 nm and probe-5'-FAM-TGAGTCCTCCGGCCCCTGAATG-TAMRA-3' (SEQ ID NO: 21) 100 nm. An ABI 7500 Taqman (ABI) was used to analyse the PCR reactions. RNA was quantified using a standard curve generated by amplification of plasmid DNA and is expressed as copies per μl of cDNA reaction.

D. Sequences

SEQ ID NO: 1
SYWIE

SEQ ID NO: 2
QILPGIGSTNYNEKFKG

SEQ ID NO: 3
GYGNYGDY

SEQ ID NO: 4
RASESVDSYGNSFM

SEQ ID NO: 5
RASNLES

SEQ ID NO: 6
QQSNEDPLT

SEQ ID NO: 7
TSGMGVG

SEQ ID NO: 8
HIWWDDVKRYNPALKS

SEQ ID NO: 9
TLPHFFDY

SEQ ID NO: 10
SASSSVSYMY

SEQ ID NO: 11
RTSNLAS

SEQ ID NO: 12
KQYHSYPPTWT

SEQ ID NO: 13
EVKVVESGADLMKPGASVKISCKATGYTFSSYWIEWVKQRPGHGLEWI
GQILPGIGSTNYNEKFKGKATFTADTSSNTAYMQLSSLTSEDSAVYYC
ARGYGNYGDYWGQGTTVTVSS

SEQ ID NO: 14
DIVLTQSPASLAVSLGQRATISCRASESVDSYGNSFMHWYQQKPGQPP
KLLIYRASNLESGIPARFSGSGSRTDFTLTINPVEADDVATYYCQQSN
EDPLTFGAGTKLELKR

SEQ ID NO: 15
QVTLKVSGPGILQPSQTLSLTCSFSGFSLNTSGMGVGWIRQPSGKGLE
WLAHIWWDDVKRYNPALKSRLTISKDTSGSQVFLKIASVDTADTATYY
CARTLPHFFDYWGQGTTLTVSS

SEQ ID NO: 16
DIQMTQSPAIMSASPGEKVTISCSASSSVSYMYWYQQKSGSSPKPWIY
RTSNLASGVPARFSGSGSGTSYSLTISSMEAEDAATYYCKQYHSYPPT
WTFGGGTKLEIKR

SEQ ID NO: 17
QVQLVQSGAEVKKPGASVKVSCKASGYTFSSYWIEWVRQAPGQGLEWI
GQILPGIGSTNYNEKFKGRVTITADTSTSTVYMELSSLRSEDTAVYYC
ARGYGNYGDYWGQGTTVTVSS

SEQ ID NO: 18
DIVLTQSPASLAVSPGQRATITCRASESVDSYGNSFMHWYQQKPGQPP
KLLIYRASNLESGVPARFSGSGSGTDFTLTINPVEAQDTANYYCQQSN
EDPLTFGAGTKLELKR

SEQ ID NO: 19
GTGAAGAGCCSCRTGTGCT

SEQ ID NO: 20
GCTSCAGGGTTAAGGTTAGCC

SEQ ID NO: 21
TGAGTCCTCCGGCCCCTGAATG

What is claimed is:

1. An isolated neutralizing IL-25 binding molecule comprising a heavy chain variable domain comprising CDR1, CDR2, and CDR3 as set forth in SEQ ID NO: 7, SEQ ID NO: 8, and SEQ ID NO: 9, and a light chain variable domain comprising CDR1', CDR2', and CDR3' as set forth in SEQ ID NO: 10, SEQ ID NO: 11, and SEQ ID NO: 12.

2. The isolated neutralizing IL-25 binding molecule of claim 1, wherein the heavy chain variable domain comprises SEQ ID NO: 15 or a variant thereof having at least 85% sequence identity to SEQ ID NO: 15.

3. The isolated neutralizing IL-25 binding molecule of claim 1, wherein the light chain variable domain comprises SEQ ID NO: 16 or a variant thereof having at least 85% sequence identity to SEQ ID NO: 16.

4. The isolated neutralizing IL-25 binding molecule of claim 1, comprising a heavy chain variable domain and a light chain variable domain, wherein the heavy chain variable domain comprises SEQ ID NO: 15 or a variant thereof having at least 85% sequence identity to SEQ ID NO: 15 and the light chain variable domain comprises SEQ ID NO: 16 or a variant thereof having at least 85% sequence identity to SEQ ID NO: 16.

5. A method of treating a rhinoviral infection, airway inflammation, inflammatory bowel disorder, psoriasis, angiogenesis, or cystic fibrosis, comprising administering a therapeutic amount of the IL-25 binding molecule of claim 1.

6. The method of claim 5, wherein the IL-25 binding molecule comprises a heavy chain variable domain comprising SEQ ID NO: 15 or a variant thereof having at least 85% sequence identity to SEQ ID NO: 15.

7. The method of claim 5, wherein the IL-25 binding molecule comprises a light chain variable domain comprising SEQ ID NO: 16 or a variant thereof having at least 85% sequence identity to SEQ ID NO: 16.

8. The method of claim 5, wherein the IL-25 binding molecule comprises a heavy chain variable domain comprising SEQ ID NO: 15 or a variant thereof having at least 85% sequence identity to SEQ ID NO: 15 and a light chain variable domain comprising SEQ ID NO: 16 or a variant thereof having at least 85% sequence identity to SEQ ID NO: 16.

\* \* \* \* \*

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: synthetic constructs

<400> SEQUENCE: 1

Ser Tyr Trp Ile Glu
1               5

<210> SEQ ID NO 2
<211> LENGTH: 17
<212> TYPE: PRT
<213> ORGANISM: Artificial Sequence
<220> FEATURE:
<223> OTHER INFORMATION: synthetic constructs

<400> SEQUENCE: 2

Gln Ile Leu Pro Gly Ile Gly Ser Thr Asn Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: synthetic constructs

<400> SEQUENCE: 3

Gly Tyr Gly Asn Tyr Gly Asp Tyr
1               5

<210> SEQ ID NO 4
<211> LENGTH: 14
<212> TYPE: PRT
<213> ORGANISM: Artificial Sequence
<220> FEATURE:
<223> OTHER INFORMATION: synthetic constructs

<400> SEQUENCE: 4

Arg Ala Ser Glu Ser Val Asp Ser Tyr Gly Asn Ser Phe Met
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthetic constructs

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic constructs

<400> SEQUENCE: 6

```
Gln Gln Ser Asn Glu Asp Pro Leu Thr
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic constructs

<400> SEQUENCE: 7

Thr Ser Gly Met Gly Val Gly
1               5

<210> SEQ ID NO 8
<211> LENGTH: 16
<212> TYPE: PRT
<213> ORGANISM: Artificial Sequence
<220> FEATURE:
<223> OTHER INFORMATION: synthetic constructs

<400> SEQUENCE: 8

His Ile Trp Trp Asp Asp Val Lys Arg Tyr Asn Pro Ala Leu Lys Ser
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: synthetic constructs

<400> SEQUENCE: 9

Thr Leu Pro His Phe Phe Asp Tyr
1               5

<210> SEQ ID NO 10
<211> LENGTH: 10
<212> TYPE: PRT
<213> ORGANISM: Artificial Sequence
<220> FEATURE:
<223> OTHER INFORMATION: synthetic constructs

<400> SEQUENCE: 10

Ser Ala Ser Ser Ser Val Ser Tyr Met Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic constructs

<400> SEQUENCE: 11

Arg Thr Ser Asn Leu Ala Ser
1               5

<210> SEQ ID NO 12
<211> LENGTH: 11
<212> TYPE: PRT
<213> ORGANISM: Artificial Sequence
<220> FEATURE:
<223> OTHER INFORMATION: synthetic constructs

<400> SEQUENCE: 12

Lys Gln Tyr His Ser Tyr Pro Pro Thr Trp Thr
```

<210> SEQ ID NO 13
<211> LENGTH: 117
<212> TYPE: PRT
<213> ORGANISM: Artificial Sequence
<220> FEATURE:
<223> OTHER INFORMATION: synthetic constructs

<400> SEQUENCE: 13

```
Glu Val Lys Val Val Glu Ser Gly Ala Asp Leu Met Lys Pro Gly Ala
1               5                   10                  15
Ser Val Lys Ile Ser Cys Lys Ala Thr Gly Tyr Thr Phe Ser Ser Tyr
            20                  25                  30
Trp Ile Glu Trp Val Lys Gln Arg Pro Gly His Gly Leu Glu Trp Ile
        35                  40                  45
Gly Gln Ile Leu Pro Gly Ile Gly Ser Thr Asn Tyr Asn Glu Lys Phe
    50                  55                  60
Lys Gly Lys Ala Thr Phe Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Ala Arg Gly Tyr Gly Asn Tyr Gly Asp Tyr Trp Gly Gln Gly Thr Thr
            100                 105                 110
Val Thr Val Ser Ser
        115
```

<210> SEQ ID NO 14
<211> LENGTH: 112
<212> TYPE: PRT
<213> ORGANISM: Artificial Sequence
<220> FEATURE:
<223> OTHER INFORMATION: synthetic constructs

<400> SEQUENCE: 14

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
            20                  25                  30
Gly Asn Ser Phe Met His Trp Tyr Gln Gln Lys Pro Gly Gln Pro Pro
        35                  40                  45
Lys Leu Leu Ile Tyr Arg Ala Ser Asn Leu Glu Ser Gly Ile Pro Ala
    50                  55                  60
Arg Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Asn
                85                  90                  95
Glu Asp Pro Leu Thr Phe Gly Ala Gly Thr Lys Leu Glu Leu Lys Arg
            100                 105                 110
```

<210> SEQ ID NO 15
<211> LENGTH: 118
<212> TYPE: PRT
<213> ORGANISM: Artificial Sequence
<220> FEATURE:
<223> OTHER INFORMATION: synthetic constructs

<400> SEQUENCE: 15

```
Gln Val Thr Leu Lys Val Ser Gly Pro Gly Ile Leu Gln Pro Ser Gln
1               5                   10                  15
```

-continued

```
Thr Leu Ser Leu Thr Cys Ser Phe Ser Gly Phe Ser Leu Asn Thr Ser
             20                  25                  30

Gly Met Gly Val Gly Trp Ile Arg Gln Pro Ser Gly Lys Gly Leu Glu
         35                  40                  45

Trp Leu Ala His Ile Trp Trp Asp Asp Val Lys Arg Tyr Asn Pro Ala
 50                  55                  60

Leu Lys Ser Arg Leu Thr Ile Ser Lys Asp Thr Ser Gly Ser Gln Val
 65                  70                  75                  80

Phe Leu Lys Ile Ala Ser Val Asp Thr Ala Asp Thr Ala Thr Tyr Tyr
                 85                  90                  95

Cys Ala Arg Thr Leu Pro His Phe Phe Asp Tyr Trp Gly Gln Gly Thr
                100                 105                 110

Thr Leu Thr Val Ser Ser
            115
```

<210> SEQ ID NO 16
<211> LENGTH: 109
<212> TYPE: PRT
<213> ORGANISM: Artificial Sequence
<220> FEATURE:
<223> OTHER INFORMATION: synthetic constructs

<400> SEQUENCE: 16

```
Asp Ile Gln Met Thr Gln Ser Pro Ala Ile Met Ser Ala Ser Pro Gly
 1               5                  10                  15

Glu Lys Val Thr Ile Ser Cys Ser Ala Ser Ser Ser Val Ser Tyr Met
             20                  25                  30

Tyr Trp Tyr Gln Gln Lys Ser Gly Ser Ser Pro Lys Pro Trp Ile Tyr
         35                  40                  45

Arg Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Lys Gln Tyr His Ser Tyr Pro Pro Thr
                 85                  90                  95

Trp Thr Phe Gly Gly Gly Thr Lys Leu Glu Ile Lys Arg
                100                 105
```

<210> SEQ ID NO 17
<211> LENGTH: 117
<212> TYPE: PRT
<213> ORGANISM: Artificial Sequence
<220> FEATURE:
<223> OTHER INFORMATION: synthetic constructs

<400> SEQUENCE: 17

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Tyr
             20                  25                  30

Trp Ile Glu Trp Val Arg Gln Ala Pro Gly Gln Gly Leu Glu Trp Ile
         35                  40                  45

Gly Gln Ile Leu Pro Gly Ile Gly Ser Thr Asn Tyr Asn Glu Lys Phe
 50                  55                  60

Lys Gly Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
```

```
                    85                  90                  95

Ala Arg Gly Tyr Gly Asn Tyr Gly Asp Tyr Trp Gly Gln Gly Thr Thr
                100                 105                 110

Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: synthetic constructs

<400> SEQUENCE: 18

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Gln Asp Thr Ala Asn Tyr Tyr Cys Gln Gln Ser Asn
                85                  90                  95

Glu Asp Pro Leu Thr Phe Gly Ala Gly Thr Lys Leu Glu Leu Lys Arg
                100                 105                 110

<210> SEQ ID NO 19
<211> LENGTH: 19
<212> TYPE: DNA
<213> ORGANISM: Artificial Sequence
<220> FEATURE:
<223> OTHER INFORMATION: synthetic constructs
<220> FEATURE:
<221> NAME/KEY: misc_feature
<222> LOCATION: (11)..(11)
<223> OTHER INFORMATION: any nucleotide
<220> FEATURE:
<221> NAME/KEY: misc_feature
<222> LOCATION: (13)..(13)
<223> OTHER INFORMATION: any nucleotide

<400> SEQUENCE: 19
gtgaagagcc ncntgtgct                                                 19

<210> SEQ ID NO 20
<211> LENGTH: 21
<212> TYPE: DNA
<213> ORGANISM: Artificial Sequence
<220> FEATURE:
<223> OTHER INFORMATION: synthetic constructs
<220> FEATURE:
<221> NAME/KEY: misc_feature
<222> LOCATION: (4)..(4)
<223> OTHER INFORMATION: any nucleotide

<400> SEQUENCE: 20
gctncagggt taaggttagc c                                              21

<210> SEQ ID NO 21
<211> LENGTH: 22
<212> TYPE: DNA
```

```
<213> ORGANISM: Artificial Sequence
<220> FEATURE:
<223> OTHER INFORMATION: synthetic constructs

<400> SEQUENCE: 21
tgagtcctcc ggcccctgaa tg                                              22
```